United States Patent [19]

Ravichandran

[11] Patent Number: 4,760,179

[45] Date of Patent: Jul. 26, 1988

[54] SUBSTITUTED AMINOXY-PROPIONAMIDES

[75] Inventor: Ramanathan Ravichandran, Yonkers, N.Y.

[73] Assignee: Ciba-Geigy Corporation, Ardsley, N.Y.

[21] Appl. No.: 848,106

[22] Filed: Apr. 4, 1986

[51] Int. Cl.[4] .......................................... C07C 103/22
[52] U.S. Cl. ................................... 564/157; 540/474;
540/553; 540/575; 544/215; 544/224; 544/335;
544/387; 548/320; 548/341; 548/378; 564/148;
564/149; 564/151; 564/164; 564/165; 564/188;
564/189; 564/191; 564/197; 524/217
[58] Field of Search ............... 564/191, 189, 164, 197,
564/148, 149, 151, 157, 165, 188

[56] References Cited

U.S. PATENT DOCUMENTS

| | | | |
|---|---|---|---|
| 3,408,422 | 10/1968 | May | 260/837 |
| 3,432,578 | 3/1969 | Martin | 260/880 |
| 3,644,278 | 2/1972 | Klemchuk | 260/45.8 N |
| 3,778,464 | 12/1973 | Klemchuk | 260/482 P |
| 3,869,278 | 3/1975 | Wilcox | 71/121 |
| 3,926,909 | 12/1975 | Wei | 260/45.85 A |
| 4,316,996 | 2/1982 | Collonge et al. | 568/784 |
| 4,386,224 | 5/1983 | Deetman | 568/703 |

OTHER PUBLICATIONS

Sashchenko et al., "Chemical Abstracts", vol. 68, 1968, Col. 93173a.
Zinner et al., Pharmazie 20 291–96, (1965).

Primary Examiner—Glennon H. Hollrah
Assistant Examiner—James H. Turnipseed
Attorney, Agent, or Firm—Harry Falber

[57] ABSTRACT

Substituted aminoxy propionamide derivatives corrsponding to the formula

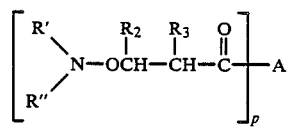

said derivatives being useful as color improvers and stabilizers in various polymeric substrates.

8 Claims, No Drawings

SUBSTITUTED AMINOXY-PROPIONAMIDES

Organic polymeric materials such as plastics and resins are subject to thermal, oxidative and photodegradation. A great variety of stabilizers are known in the art for stabilizing a diversity of substrates. Their effectiveness varies depending upon the causes of degradation and the substrate stabilized. In general, it is difficult to predict which stabilizer will be most effective and most economical for any one area of application. For example, stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of discoloration may require inhibiting reactions which yield new chromophores or color bodies in the substrate or stabilizer. Problems of process stability and incompatibility must also be considered.

Various organic hydroxylamine compounds are generally known and some are commercially available. A number of patents disclose nitrogen-substituted hydroxylamines as antioxidant stabilizers for various substrates including polyolefins, polyesters and polyurethanes. U.S. Pat. Nos. 3,432,578, 3,644,278, 3,778,464, 3,408,422, 3,926,909, 4,316,996 and 4,386,224 are representative of such patents which basically disclose N,N-dialkyl-, N,N-diaryl and N,N-diaralkyl hydroxylamine compounds and their color improvement and color stabilizing activity. Several carbamoyl-substituted hydroxylamine compounds are disclosed in U.S. Pat. No. 3,869,278 and Zinner et al, Pharmazie 20, 291 (1965) is a non-polymeric context.

It has now been determined that the substituted aminoxy propionamides of this invention exhibit a variety of desirable properties which makes them particularly effective and useful as stabilizers. Thus, the compounds serve to protect various substrates such as polyolefins, elastomers and lubricating oils against the adverse effects of oxidative and thermal degradation. They are most effective as color improvers and process stabilizers in polyolefin compositions which may contain metal salts of fatty acids and which also contain a phenolic antioxidant. Thus, they serve to substantially reduce color formation resulting from the presence of the phenolic antioxidant and/or from the processing conditions as well as to directly protect the polymer from said processing conditions. They also prevent the discoloration of polyolefin compositions containing hindered amine light stabilizers or combinations of phenolic antioxidants and organic phosphites. In addition, the gas fading that may be experienced upon exposure to the combustion products of natural gas is also significantly reduced.

It is the primary object of this invention to provide a class of propionamide derivatives which exhibits a broad range of improved stabilization performance characteristics.

Various other objects and advantages of this invention will become evident from the following description thereof.

The compounds of this invention correspond to the formula

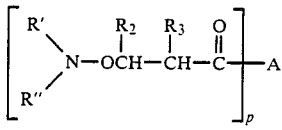

wherein
p is 1 to 4;
R' and R" are independently hydrogen, alkyl of 1 to 36 carbon atoms, cycloalkyl of 5 to 12 carbon atoms, aralkyl of 7 to 9 carbon atoms or said aralkyl substituted by alkyl of 1 to 36 carbon atoms,
$R_2$ and $R_3$ are independently hydrogen or alkyl of 1 to 12 carbon atoms;
A, when p=1, is a group $NHR_4$, wherein $R_4$ is hydrogen, amino, alkyl of 1 to 18 carbon atoms or

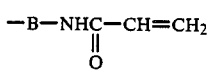

and B is a direct bond or alkylene of 1 to 10 carbon atoms;
A, when p=2, is a bivalent radical of a 5–7 membered heterocyclic compound containing two nitrogen atoms in the ring, with the free valencies on the nitrogen atoms, or is a group

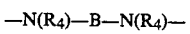

and B and $R_4$ have the meanings given above;
A, when p=3, is a group of the formula

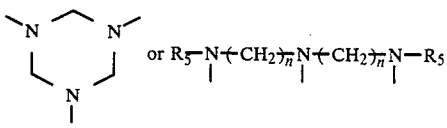

and n is 2 to 6 and $R_5$ is hydrogen or alkyl of 1 to 4 carbon atoms; and
A, when p=4, is a group of the formula

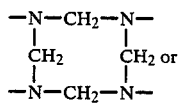

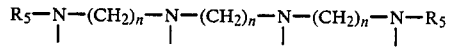

and $R_5$ and n have the meanings given above.

The R' and R" groups are preferably hydrogen, straight-chain or branched alkyl with 1 to 18 carbon atoms such as methyl, ethyl, n-propyl, n-butyl, tert-butyl, n-pentyl, n-octyl, 2-ethylhexyl, decyl, dodecyl and octadecyl; cyclopentyl and cyclohexyl; and benzyl, α-methylbenzyl and α,α-dimethyl-benzyl. $R_2$ and $R_3$ are preferably hydrogen or alkyl of 1 to 4 carbon atoms.

Other preferred groups include, for p=1, $R_4$ as $C_1$–$C_{18}$ alkyl (see list for R' and R") and B as $C_1$–$C_6$ alkylene; for p=2, A as

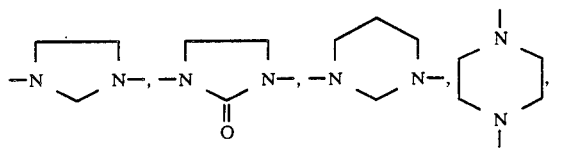

$R_4$ as hydrogen and B as straight chain $C_1$–$C_6$ alkylene; and for p=3,

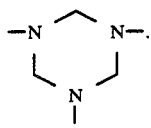

A as

The derivatives of this invention wherein p is 1 can be prepared by reacting the appropriately substituted hydroxylamine with an appropriately substituted acrylamide in a solvent to yield the desired product. Typical acrylamides include acrylamide, methacrylamide, N-tert.butylacrylamide, N-tert.octylacrylamide and N,N-methylenebisacrylamide. The solvent can be an aromatic hydrocarbon such as benzene, toluene, xylene, and the like, or a heterocyclic ether, such as tetrahydrofuran. The reaction temperature ranges from 65° to 135° C. The preferred method for preparing these p=1 compounds involves reacting the hydroxylamine with the acrylamide in the presence of an alkali hydroxide or an alkali alkoxide. The starting materials needed to prepare the stabilizers of this invention are items of commerce or can be prepared by known methods.

The derivatives of this invention wherein p is 2–4 can be prepared by reacting the appropriately substituted 3-(N,N-di-substituted-aminoxy)-propionic acid with a chloride such as oxalyl chloride or thionyl chloride, to prepare the corresponding acid chloride and then reacting the acid chloride with the appropriate amine or nitrogen-containing heterocyclic compound. Typical reactants to prepare p=2 compounds include pyrazolidine, imidazolidine, ethylenediamine, hexamethylenediamine, N,N'-dimethylhexamethylene diamine, piperazine and methylhydrazine; for p=3 compounds include diethylenetriamine and s-hexahydro triazine; and for p=4 compounds include triethylenetetramine.

The propionic acid derivatives noted above are prepared by the saponification of the correspondinq ester, the latter ester being derived from the reaction of di-substituted hydroxylamines and the appropriate acrylate.

The compounds of the present invention are particularly effective in stabilizing organic materials subject to oxidative, thermal and actinic degradation, such as plastics, polymers and resins.

Substrates in which these compounds are particularly useful are polyolefins such as polyethylene and polypropylene; polystyrene, including impact polystyrene, ABS resin, SBR, isoprene, as well as natural rubber, polyesters including polyethylene terephthalate and polybutylene terephthalate, including copolymers, and lubricating oils such as those derived from mineral oil.

In general polymers which can be stabilized include
1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.
2. Mixtures of the polymers mentioned under 1), for example mixtures of polypropylene with polyisobutylene.
3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.
4. Polystyrene, poly-(p-methylstyrene).
5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.
6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.
7. Halogen-containing polymers, such as polychloroprene, chlorinated rubbers, chlorinated or sulfochlorinated polyethylene, epichlorohydrine homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.
8. Polymers which are derived from α,β-unsaturated acids and derivatives thereof, such as polyacrylates and polymethacrylates, polyacrylamide and polyacrylonitrile.
9 Copolymers from the monomers mentioned under 8) with each other or with other unsaturated monomers, such as, for instance, acrylonitrile/butadien, acrylonitrile/alkyl acrylate, acrylonitrile/alkoxyalkyl acrylate or acrylo-nitrile/vinyl halogenide copolymers or acrylonitrile/alkyl methacrylate/butadiene terpolymers.
10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadiens with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamid or poly-m-phenylene isophthalamide, as well as copolymers thereof with polyethers, such as for instance with polyethylene qlycol, polypropylene qlycol or polytetramethylene qlycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane]terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymerhomologous manner, such as cellulose acetates, cellulose propionates and cellulose butyrates, or the cellulose ethers, such as methylcellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellithates) and also mixtures of synthetic esters with mineral oils in ay weight ratios, which materials may be used as plasticizer for polymers or as textile spinning oils, as well as aqueous emulsions of such materials.

29. Aqueous emulsions of natural or synthetic rubber, e.g. natural latex or latices of carboxylated styrene/butadiene copolymers.

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants 1.1. Alkylated monophenols, for example, 2,6-di-tert.butyl-4-methylphenol
2-tert.butyl-4,6-dimethylphenol
2,6-di-tert.butyl-4-ethylphenol
2,6-di-tert.butyl-4-n-butylphenol
2,6-di-tert.butyl-4-i-butylphenol
2,6-di-cyclopentyl-4-methylphenol
2-($\alpha$-methylcyclohexyl)-4,6-dimethylphenol
2,6-di-octadecyl-4-methylphenol
2,4,6-tri-cyclohexylphenol
2,6-di-tert.butyl-4-methoxymethylphenol 1.2. Alkylated hydroquinones, for example, 2,6-di-tert.butyl-4-methoxyphenol
2,5-di-tert.butyl-hydroquinone
2,5-di-tert.amyl-hydroquinone
2,6-diphenyl-4-octadecyloxyphenol 1.3. Hydroxylated thiodiphenyl ethers, for example 2,2'-thio-bis-(6-tert.butyl-4-methylphenol)
2,2'-thio-bis-(4-octylphenol)
4,4'-thio-bis-(6-tert.butyl-3-methylphenol)
4,4'-thio-bis-(6-tert.butyl-2-methylphenol)

1.4. Alkyliden-bisphenols, for example, 2,2'-methylene-bis-(6-tert.butyl-4-methylphenol)
2,2'-methylene-bis-(6-tert.butyl-4-ethylphenol)
2,2'-methylene-bis-[4-methyl-6-($\alpha$-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-($\alpha$-methylbenzyl)-4-nonylphenol]
2,2'-methylene-bis-[6-($\alpha$,$\alpha$-dimethylbenzyl)-4-nonylphenol]

2,2'-methylene-bis-(4,6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6-tert.butyl-2-methylphenol)
1,1-bis-(5-tert.butyl-4-hydroxy-2-methylphenyl-butane
2,6-di-(3-tert.butyl-5-methyl-2-hydroxybenzyl)-4-methylphenol
1,1,3-tris-(5-tert.butyl-4-hydroxy-2-methylphenyl)-butane
1,1-bis-(5-tert.butyl-4-hydroxy-2-methylphenyl)-3-n-dodecylmercaptobutane
ethylenglycol-bis-[3,3-bis-(3'-tert.butyl-4'-hydroxyphenyl)-butyrat]
di-(3-tert.butyl-4-hydroxy-5-methylphenyl)-dicyclopentadien
di-[2-(3'-tert.butyl-2'-hydroxy-5'-methyl-benzyl)-6-tert.butyl-4-methylphenyl]-terephthalate.

1.5. Benzyl compounds, for example, 1,3,5-tri-(3,5-di-tert.butyl-4-hydroxybenzyl)-2,4,6-trimethylbenzene-di-(3,5-di-tert.butyl-4-hydroxybenzyl)-sulfide
3,5-di-tert.butyl-4-hydroxybenzyl-mercapto-acetic acid isooctyl ester
bis-(4-tert.butyl-3-hydroxy-2,6-dimethylbenzyl)dithiol-terephthalate
1,3,5-tris-(3,5-di-tert.butyl-4-hydroxybenzyl)-isocyanurate
1,3,5-tris-(4-tert.butyl-3-hydroxy-2,6-dimethylbenzyl)-isocyanurate
3,5-di-tert.butyl-4-hydroxybenzyl-phosphoric acid-dioctadecyl ester
3,5-di-tert.butyl-4-hydroxybenzyl-phosphoric acid-monoethyl ester, calcium-salt

1.6. Acylaminophenols, for example, 4-hydroxy-lauric acid anilide
4-hydroxy-stearic acid anilide
2,4-bis-octylmercapto-6-(3,5-tert.butyl-4-hydroxyanilino)-s-triazine
octyl-N-(3,5-di-tert.butyl-4-hydroxypheyl)-carbaminate

1.7. Esters of
β-(3,5-di-tert.butyl-4-hydroxyphenyl)-propionic acid with monohydric or polyhydric alcohols, for example, methanol
octadecanol
1,6-hexanediol
neopentylglycol
thiodiethyleneglycol
diethyleneglycol
triethyleneglycol
pentaerythritol
tris-hydroxyethyl isocyanurate
di-hydroxyethyl oxalic acid diamide

1.8. Ester of
β-(5-tert.butyl-4-hydroxy-3-methylphenyl)-propionic acid with monohydric or polyhydric alcohols, for example, methanol
octadecanol
1,6-hexanediol
neopentylglycol
thiodiethyleneglycol
diethyleneglycol
triethyleneglycol
pentaerytritol
tris-hydroxyethyl isocyanorate
di-hydroxyethyl oxalic acid diamide

1.9. Amides of
β-(3,5-di-tert.butyl-4-hydroxyphenyl)-propionic acid for example, N,N'-di-(3,5-di-tert.butyl-4-hydroxyphenylpropionyl)-hexamethylendiamine
N,N'-di-(3,5-di-tert.butyl-4-hydroxyphenylpropionyl)-trimethylendiamine  N,N'-di-(3,5-di-tert.butyl-4-hydroxyphenylpropionyl)-hydrazine

2. UV absorbers and liqht stabilisers 2.1. 2-(2'-Hydroxyphenyl)-benztriazoles, for example, the 5'-methyl-, 3',5'-di-tert.butyl-, 5'-tert.butyl-, 5'-(1,1,3,3-tetramethylbutyl)-, 5-chloro-3',5'-di-tert.butyl-, 5-chloro-3'-tert.butyl-5'-methyl-, 3'-sec.butyl-5'-tert.butyl-, 4'-octoxy, 3',5'-di-tert.amyl-, 3',5'-bis-(α,α,α-dimethylbenzyl)-derivative.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivative.

2.3. Ester of optionally substituted benzoic acids for example, phenyl salicylate, 4-tert.butyl-phenylsalicilate, octylphenyl salicylate, dibenzoylresorcinol, bis-(4-tert.butylbenzoyl-resorcinol, benzoylresorcinol, 3,5-di-tert.butyl-4-hydroxybenzoic acid 2,4-di-tert.butyl-phenyl ester and 3,5-di-tert.-butyl-4-hydroxybenzoic acid hexadecyl ester.

2.4. Acrylates, for example, α-cyano-β,β-diphenylacrylic acid ethyl ester or isooctyl ester, α-carbomethoxycinnamic acid methyl ester, α-cyano-β-methyl-p-methoxy-cinnamic acid methyl ester or butyl ester, α-carbomethoxy-p-methoxycinnamic acid methyl ester, N-(β-carbomethoxy-β-cyanovinyl)-2-methylindoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclo-hexyl-di-ethanolamine, nickel dibutyldithiocarbamate, nickel salts of 4-hydroxy-3,5-di-tert.butylbenzylphosphonic acid monoalkyl esters, such as of the methyl, ethyl or butyl ester, nickel complexes of ketoximes such as of 2-hydroxy-4-methylphenyl undecyl ketoxime, nickel complexes of 1-phenyl-4-lauroyl-5-hydroxy-pyrazol, optionally with additional ligands.

2.6. Sterically hindered amines, for example bis-(2,2,6,6-tetramethylpiperidyl)-sebacate  bis-(1,2,2,6,6-pentamethylpiperidyl)-sebacate n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylendiamine and 4-tert.octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethylpiperazinone).

2.7. Oxalic acid diamides, for example, 4,4'-di-octyloxyoxanilide, 2,2'-di-octyloxy-5,5'-di-tert.butyl-oxanilide, 2,2'-di-dodecyloxy-5,5'-di-tert.butyl-oxanilide, 2-ethoxy-2'-ethyl-oxanilide, N,N'-bis (3-dimethylaminopropyl)-oxalamide, 2-ethoxy-5-tert.butyl- 2'-ethyloxanilide and its mixture with 2-ethoxy-2'-ethyl-5,4'-di-tert.butyloxanilide and mixtures of ortho- and para-methoxy-as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert.butyl-4-hydroxyphenylpropionyl)-hydrazine, 3-salicyloylamino-1,2,4-triazole, bis-benzyliden-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearyl-pentaerythrit diphosphite, tris-(2,4-di-tert.butylphenyl) phosphite, di-isodecylpentaerythritol diphosphite, di-(2,4-di-tert.butylphenyl)pentaerythritol diphosphite, tristearyl-sorbite triphosphite, tetrakis-(2,4-di-tert.butylphenyl)-4,4'-diphenylylendiphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythritol-tetrakis-(β-dodecylmercapto)-propionate.

6. Polyamide stabilisers, for example copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. Other additives, for example, plasticizers, lubricants, emulsifiers, pigments, optical brighteners, flameproofing agents, anti-static agents, blowing agents and thiosynergists such as dilaurylthiodipropionate or distearylthiodipropionate.

While the instant propionamides can be beneficially used as stabilizers for a variety of substrates, particularly the polyolefins, both alone and in conjunction with other coadditives, the introduction of the instant propionamides into polyolefins, optionally containing various alkali metal, alkaline earth metal and aluminum salts of higher fatty acids (see Additive #7 hereinabove), with hindered phenolic antioxidants exhibits enhanced and particularly salubrious protection to such substrates in terms of reducing color formation stemming from the presence of the phenols. Such phenolic antioxidants include n-octadecyl 3,5-di-tert-butyl-4-hydroxyhydrocinnamate, neopentanetetrayl tetrakis-(3,5-di-tert-butyl-4-hydroxyl-hydrocinnamate),di-n-octadecyl 3,5-di-tert-butyl-4-hydroxybenzyl-phosphonate, 1,3,5-tris(3,5-di-tert-butyl-4-hydroxy-benzyl)isocyanurate, thiodiethylene bis(3,5-di-tert-butyl-4-hydroxyhydrocinnamate), 1,3,5-trimethyl-2,4,6-tris (3,5-di-tert-butyl-4-hydroxybenzyl)benzene, 3,6-di-oxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris-(2,6-di-methyl-4-tert-butyl-3-hydroxybenzyl)isocyanurate, 1,1,3-tris-(2-methyl-4-hydroxy-5-tert-butylphenyl)butane, 1,3,5-tris-[2-(3,5-di-tert-butyl-4-hydroxyhydrocinnamoyloxy)-ethyl]-isocyanurate, 3,5-di-(3,5-di-tert-butyl-4-hydroxybenzyl)-mesitol, hexa-methylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl-3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis-[2-(3,5-tert-butyl-4-hydroxyhydroxo-cinnamoyloxy)ethyl]-oxamide, and preferably neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris-(3,5-di-tert-butyl-4-hydroxybenzyl)isocyanurate, 2,6-di-tert-butyl-p-cresol or 2,2'-ethylidene-bis(4,6-di-tert-butylphenol).

Likewise, the instant compounds prevent color formation when hindered amine light stabilizers are present, such hindered amines including bis(1,2,2,6,6-pentamethyl-4-piperidyl)-2-n-butyl-2-(3,5-di-tert-butyl-4-hydroxybenzyl) malonate; bis(2,2,6,6-tetramethyl-4-piperidyl) sebacate; dimethylsuccinate polymer with 4-hydroxy-2,2,6,6-tetramethyl-1-piperidinethanol; and polymer of 2,4-dichloro-6-octylamino-s-triazine with N'-(2,2,6,6-tetramethyl-4-piperidyl)hexamethylene diamine.

The following examples illustrate the embodiments of this invention. In these examples, all parts given are by weight unless otherwise specified.

EXAMPLE I

N-tert-butyl-[3-(N,N-dibenzylaminoxy)-propionamide]

A solution of 21.33 g of dibenzylhydroxylamine in 100 ml of dry tetrahydrofuran is admixed with 1.12 g of potassium-tert-butoxide followed by 12.70 g of N-tert-butylacrylamide. The solution is heated under reflux for 24 hours under $N_2$. The crude reaction mixture is concentrated under reduced pressure and the residue is partitioned between water and methylene chloride. The organic layer is washed with water, brine dried ($MgSO_4$) and evaporated under reduced pressure. Purification by liquid chromatography affords the title compound as an oil.

Anal. calcd. for $C_{21}H_{28}N_2O_2$: C, 74.1; H, 8.3; N, 8.2. Found: C, 74.3; H, 8.5; N, 8.3.

EXAMPLE II

N-tert-octyl-[3-(N,N-dibenzylaminoxy)-propionamide]

The procedure of Example I is repeated using 23.31 g of dibenzylhydroxylamine, 1.23 g of potassium-tert-butoxide and 20.0 g of N-tert-octylacrylamide in 100 ml of dry tetrahydrofuran to afford the title compound as a white crystalline solid: mp 96°–98° C.

Anal. calcd. for $C_{24}H_{36}N_2O_2$: C, 75.0; H, 9.4; N, 7.3. Found: C, 75.6; H, 9.1; N, 7.2.

of 7 to 9 carbon atoms or said aralkyl substituted by alkyl of 1 to 36 carbon atoms, R' also being hydrogen;

$R_2$ and $R_3$ are independently hydrogen of alkyl of 1 to 12 carbon atoms;

A, when p=1, is a group $NHR_4$, wherein $R_4$ is hydrogen, amino, alkyl of 1 to 18 carbon atoms or

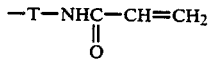

and T is a direct bond alkylene of 1 to 10 carbon atoms;

A, when p=2, is a group

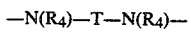

and T and $R_4$ have the meanings given above;

A, when p=3, is a group of the formula

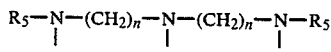

and n is 2 to 6 and $R_5$ is hydrogen or alkyl of 1 to 4 carbon atoms; and

A, when p=4, is a group of the formula

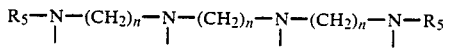

and $R_5$ and n have the meanings given above.

2. The compound of claim 1, wherein R' and R" are independently straight-chain or branched alkyl with 1 to 18 carbon atoms, cyclopentyl, cyclohexyl, benzyl, α-methylbenzyl or α,α-dimethylbenzyl and $R^2$ and $R^3$ are independently hydrogen or alkyl of 1 to 4 carbon atoms.

3. The compound of claim 2, wherein R' and R" are benzyl are $R^2$ and $R^3$ are hydrogen.

4. The compound of claim 1, wherein p is 1 and $R_4$ is $C_1$-C18 alkyl.

5. N-tert-butyl-[3-(N,N-dibenzylaminoxy)propionamide] according to claim 1.

6. N-tert-octyl-[3-(N,N-dibenzylaminoxy)propionamide] according to claim 1.

7. N,N'-Dimethyl-N,N'-hexamethylene-bis-[3-(N,N-dibenzylaminoxy)propionamide] according to claim 1.

8. N-tert-octyl-[3-(N,N-diethylaminoxy)propionamide] according to claim 1.

* * * * *